US009526818B2

(12) United States Patent
Kearsley et al.

(10) Patent No.: US 9,526,818 B2
(45) Date of Patent: Dec. 27, 2016

(54) PROTECTIVE CAP FOR DRIVELINE CABLE CONNECTOR

(71) Applicant: THORATEC CORPORATION, Pleasanton, CA (US)

(72) Inventors: Keith Hamilton Kearsley, Burlington, MA (US); Gabe Wegel, Maynard, MA (US); Kathryn B. Frederick, Medford, MA (US); Julien Duhamel, Billerica, CA (US); Brian Barber, Napa, CA (US)

(73) Assignee: THORATEC CORPORATION, Pleasanton, CA (US)

( * ) Notice: Subject to any disclaimer, the term of this patent is extended or adjusted under 35 U.S.C. 154(b) by 0 days.

(21) Appl. No.: 14/687,805

(22) Filed: Apr. 15, 2015

(65) Prior Publication Data

US 2015/0290377 A1    Oct. 15, 2015

Related U.S. Application Data

(60) Provisional application No. 61/980,034, filed on Apr. 15, 2014, provisional application No. 62/044,909, filed on Sep. 2, 2014.

(51) Int. Cl.
| H01R 13/44 | (2006.01) |
| A61M 1/12 | (2006.01) |
| A61M 39/02 | (2006.01) |
| A61M 1/10 | (2006.01) |
| A61M 39/20 | (2006.01) |

(52) U.S. Cl.
CPC ............ *A61M 1/122* (2014.02); *A61M 1/1008* (2014.02); *A61M 39/0208* (2013.01); *A61M 39/0247* (2013.01); *A61M 39/20* (2013.01); *A61M 2039/0258* (2013.01); *A61M 2039/0288* (2013.01)

(58) Field of Classification Search
CPC ...... A61M 1/122; A61M 1/1008; A61M 1/12; A61M 1/10; A61M 39/0247; A61M 39/0208; A61M 39/20; A61M 39/02; A61M 2039/0258; A61M 2039/0288
USPC .................... 439/135, 909, 136; 49/465, 506
See application file for complete search history.

(56) References Cited

U.S. PATENT DOCUMENTS

| 2,428,323 A | 9/1947 | Winer |
| 5,695,471 A | 12/1997 | Wampler |
| 5,708,346 A | 1/1998 | Schöb |
| 5,888,242 A | 3/1999 | Antaki et al. |

(Continued)

*Primary Examiner* — Javaid Nasri
(74) *Attorney, Agent, or Firm* — Kilpatrick Townsend & Stockton LLP

(57) ABSTRACT

A protective cap for fluidly sealing a connector of a cable is provided. The protective cap includes a flexible body having an interior cavity with a distal opening through which the connector is inserted. The distal opening is defined by an annular ridge that engages a cable portion proximal the connector to fluidly seal the entire connector within the cavity. The body portion may have an oval-shaped cross-section while the interior cavity is cylindrical so that the portions wider portions of the body provide longitudinal rigidity to facilitate installation and removal of the cap by a manual pushing and pulling. A tether may be included to attach the cap to a distal portion of the cable. The protective cap and tether may be integrally formed of a soft, highly flexible material to improve ease of use, biocompatibility and patient comfort.

34 Claims, 13 Drawing Sheets

(56) References Cited

U.S. PATENT DOCUMENTS

| | | |
|---|---|---|
| 6,053,705 A | 4/2000 | Schöb et al. |
| 6,065,981 A | 5/2000 | Sopotnick et al. |
| 6,071,093 A | 6/2000 | Hart |
| 6,100,618 A | 8/2000 | Schoeb et al. |
| 6,116,862 A | 9/2000 | Rau et al. |
| 6,186,665 B1 | 2/2001 | Maher et al. |
| 6,222,290 B1 | 4/2001 | Schöb et al. |
| 6,234,772 B1 | 5/2001 | Wampler et al. |
| 6,249,067 B1 | 6/2001 | Schob et al. |
| 6,264,635 B1 | 7/2001 | Wampler et al. |
| 6,278,251 B1 | 8/2001 | Schöb |
| 6,351,048 B1 | 2/2002 | Schob et al. |
| 6,355,998 B1 | 3/2002 | Schöb et al. |
| 6,634,224 B1 | 10/2003 | Schöb et al. |
| 6,688,861 B2 | 2/2004 | Wampler |
| 6,879,074 B2 | 4/2005 | Amrhein et al. |
| 6,991,595 B2 | 1/2006 | Burke et al. |
| 7,112,903 B1 | 9/2006 | Schob |
| 7,547,218 B2 | 6/2009 | Hiew et al. |
| 7,699,586 B2 | 4/2010 | LaRose et al. |
| 7,771,221 B1 * | 8/2010 | Blackwell ............... H01R 13/52 439/282 |
| 7,918,609 B2 | 4/2011 | Melton et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,493 B2 | 4/2012 | LaRose et al. |
| 8,323,174 B2 | 12/2012 | Jeevanandam et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,652,024 B1 | 2/2014 | Yanai et al. |
| 8,657,733 B2 | 2/2014 | Ayre et al. |
| 8,668,473 B2 | 3/2014 | LaRose et al. |
| 8,794,989 B2 | 8/2014 | Kearsley et al. |
| 2005/0020111 A1 | 1/2005 | Pagac |
| 2005/0071001 A1 | 3/2005 | Jarvik |
| 2006/0010737 A1 | 1/2006 | Lee |
| 2007/0078293 A1 | 4/2007 | Shambaugh, Jr. et al. |
| 2008/0021394 A1 | 1/2008 | LaRose et al. |
| 2009/0203957 A1 | 8/2009 | LaRose et al. |
| 2012/0046514 A1 | 2/2012 | Bourque |
| 2012/0095281 A1 | 4/2012 | Reichenbach et al. |
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |

* cited by examiner

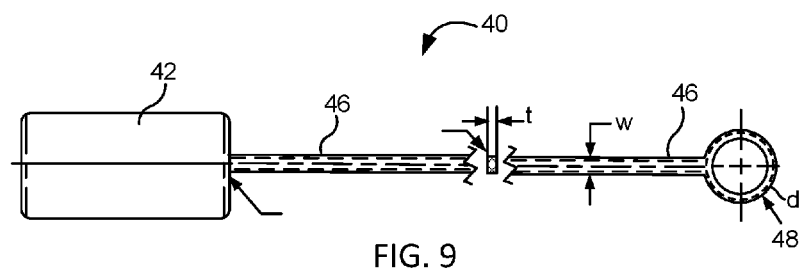
FIG. 9
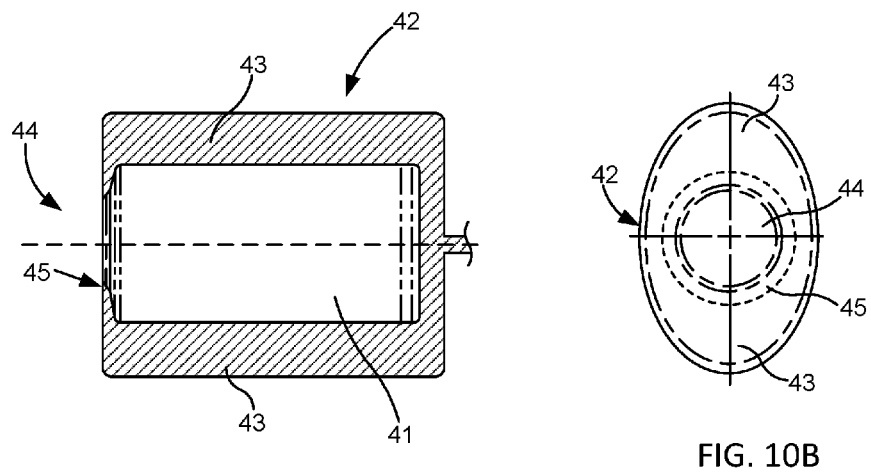
FIG. 10A
FIG. 10B

PROTECTIVE CAP FOR DRIVELINE CABLE CONNECTOR

CROSS-REFERENCES TO RELATED APPLICATIONS

The present application is a non-provisional of and claims the benefit of priority of U.S. Provisional Patent Application No. 61/980,034 filed Apr. 15, 2014 and U.S. Provisional Application No. 62/044,909 filed Sep. 2, 2014, each of which is incorporated herein by reference in its entirety.

BACKGROUND OF THE INVENTION

This application relates generally to mechanical circulatory support systems, and more specifically relates to a protective cap or cover for a connector of a driveline cable for an implantable blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

The VAD is powered and may also be controlled by a driveline cable that extends from the VAD and through an aperture of the patient to an external power source and/or controller device. The driveline cable terminates in a connector having a connector adapted to connect to a corresponding connector receptacle of an external power source/control unit worn by the patient. The connector includes a group of electrical contacts that electrically engage with a corresponding group of electrical contacts within the receptacle when connected. During implantation of the VAD, a connector of an associated driveline cable used to power and control the device may be exposed to fluids, such as saline or other fluids, or debris which may damage or degrade its internal components. In some devices, after implantation of the VAD, the connector may periodically be detached from the power source by the patient for various purposes, for example when the patient showers or bathes. It is desirable to protect the connector of the driveline cable from exposure to fluids or other debris when the connector is detached from the power source. It would further desirable to provide such protection and sealing of the connector in a manner that is effective, durable, and user friendly, particularly for patients that are elderly or of compromised health.

BRIEF SUMMARY OF THE INVENTION

The invention provides a cap or cover that protects and seals a connector of a driveline cable, in particular an in-line connector that connects a modular external portion of the driveline with a percutaneous portion of the driveline cable. In one aspect, the protective cap is configured to be easily pushed on the proximal connector of the modular external driveline cable by the surgeon so that the connector is contained within an internal cavity and sealed from intrusion of fluid or debris onto the electrical contacts of the connector in the operating room during implantation of the device and connection of the driveline cable by the surgeon. In another aspect, the cap may be configured for use with an external connector of the driveline by the patient or medical professional for various other purposes, such as showering. In one aspect, the cap is fabricated from a resilient, flexible material, such as silicone, so as to allow the cap to stretch when being pushed onto the connector, and a flexible ridge that forms a fluid seal when the connector is disposed within the internal cavity of the protective cap. In another aspect, the cap includes one or more features adapted to prevent any residual fluid deposits at or near the flexible ridge from being drawn into the cavity and splashing the electrical contacts as the cap is removed (e.g. due to suction). This may be accomplished by shielding components from fluid splash, directing fluid splash away from components or by reducing any suction created so as to avoid or reduce any splashing from any residual fluid remaining near the seal interface. The features may include any or all of: dimensioning or shaping of the cavity, one or more ridges, air flow ports to reduce suction, absorbent material to absorb any splashed fluid, various tightening mechanisms adapted to reduce suction during removal, tape or grease to prevent trapped water, and more. The air flow ports may be plugged, such as with a removable elastomeric plug, so that removable of the plug relieves any build-up in suction or the air flow ports may be formed by puncturing a membrane before connecting the plug.

In certain aspects, the cap includes a closed cavity with a single distal opening through which the connector can be inserted. The distal opening stretches over the connector to receive at least a distal portion of the connector including the electrical contacts and internal components and forms a fluid seal around a more proximal portion of the cable or connector so as to prevent water ingress into the cavity while the distal portion of the connector remains sealed within. As described herein, distal refers to the terminal end of the referenced connector. It is appreciated that when used in reference to an in-line connector of the driveline cable, the terms distal and proximal are in relation to the respective connector which may be different from the proximal and distal ends of the entire driveline when connected.

In certain aspects, the cavity of the cap is dimensioned to receive the connector or a distal portion thereof. For example, the cavity may approximately cylindrical in shape to receive a substantially cylindrical connector. In one aspect, the cavity of the cap is dimensioned to envelop the entire connector, thereby precluding the possibility of wetting of the sensitive internal components of the connector. It is appreciated, that the cavity may dimensioned in various sizes and shapes and with various clearance tolerances to correspond to a particular geometry of a corresponding connector. Alternatively, the cavity may be dimensioned with sufficient clearance so as to allow insertion of connectors of differing sizes or shapes, the sealing aspect being provided by the fit of the distal opening on a more proximal portion of the connector or cord. In one aspect, the distal opening is dimensioned to seal with an outer surface of the cord proximal of the connector plug so that the flexible ridge seal that sealingly engages the outer surface of a cable portion proximal the connector so as to fluidly seal the entire connector within the cavity of the protective cap. The proximal cord portion may be the cable itself or an associated boot member disposed thereon. In certain embodiments, the diameter of the distal opening is about the same or smaller than the outside diameter of the proximal cord portion so that the flexible ridge engages the cord surface entirely around the proximal cord portion sufficiently to provide a fluid seal. Utilizing a distal opening that is slightly smaller allows the flexible ridge to remain slightly deflected when engaged with the proximal cord portion so as to provide an increased sealing force about the proximal cord portion sufficient to prevent intrusion of fluid into the sealed cavity. In another aspect, the connector may include a ridge or recess on a proximal portion thereof that is dimensioned to sealingly engage with the flexible ridge at or near the distal opening of the protective cap.

To provide improved sealing of the connector within the cavity, the distal opening may be defined by a flexible ridge that extends inwardly toward the longitudinal axis of the protective cap along which the connector is inserted. The flexible ridge deflects or stretches as the connector is inserted, the resilience of the flexible ridge providing the required sealing force. In one aspect, the flexible ridge is an annular ridge that circumscribes the distal opening of a cylindrical cavity, thereby allowing installation and removal by a pushing and pulling movement, without requiring twisting or screwing along corresponding threads or manipulator of various other sealing mechanisms. The protective cap and the flexible ridge may be integrally formed of a soft, highly flexible materials (e.g. an elastic polymer) so as to be sufficiently flexible to allow passage of the connector through the distal opening, but sufficiently resilient so as to provide a sealing force about a proximal portion of the connector (such as an associated boot member) or a portion of the cable proximal the connector.

To facilitate installation and removal of the protective cap and the connector by a manual push-pull movement, the protective cap is fabricated, entirely or at least in part, from a flexible material to allow the distal opening to easily stretch over the connector and one or more reinforcing portions that provide longitudinal rigidity to the protective cap while being pushed on or pulled from the protective cap. This is advantageous since a cap of flexible material could easily deform during installation or removal making installation and removal of the cap unnecessarily difficult. In one aspect, the one or more reinforcing portions comprise one or more portions having increased width laterally from the longitudinal axis of the protective cap along which the connector is inserted. The one or more portions may be included on opposite sides of the protective cap so as to support the overall shape of the cap during installation and removal. In one aspect, the outer shape of the cap is oval in cross-section and the interior cavity is substantially cylindrical such that reinforcing portions are defined by opposite ends of the oval cross section. This outside oval shape is advantageous as it defines the reinforcing portions on each side of the protective cap while the thin axis of the oval allows for a lower profile and smaller packaging.

In another aspect, the protective cap, including a body portion having an interior cavity with a single distal opening around which extends a flexible ridge, is formed as a single integral piece from a common material. This configuration allows for easy and intuitive installation and removal and prevents water ingress into the cavity when the connector is received within. By forming the protective cap as a single integral piece, the fabrication of the cap is simplified and the longevity and durability of the cap is increased as compared to a cap constructed from multiple or separate components.

In certain aspects, the protective cap may also include a tether for attaching the cap to a distal portion of the cable so that the cap remains near the connector when not in use so as to be readily available to a user when needed. The tether is attached to the body portion of the cap at one end and attached to a portion of the cable proximal the connector. The tether may include a coupling feature, such as a ring or snap fit component, for coupling with the cable. The coupling feature may attach the tether at a particular location or may be dimensioned so as to be slidable along the cable. The tether is of sufficient length so that the protective cap can be pushed over the connector until the flexible ridge seals about a proximal portion of the connector (e.g. a sloped boot portion) or a portion of the cable proximal the connector. In some embodiments, the tether may be a simple thread or similar member that is tied or attached to the cable and tied to the cap. In other embodiments, the tether and protective cap may also be formed as one integral piece, thereby increasing the longevity and durability of the connection between tether and the protective cap. In contrast, multi-component assemblies may be less reliable, more difficult to seal, harder to user and less cost-effective to produce. In embodiments using a tether so that the cap remains attached to the cable, it is advantageous that the cap be formed entirely of a soft and highly flexible material since the cap would remain situated near the patient's abdomen and may periodically be felt by the patient. Such a configuration allows the cap to remain near the connector end at all times and to be readily accessible to the user, thereby improving patient compliance in protecting the connector when disconnected. Conventional caps that are formed of hard plastics would likely cause patient discomfort if maintained near the patient's abdomen, such that a patient would be more likely to remove and/or misplace such a cap. In another aspect, the protective cap, with or without a tether, can be fabricated from a brightly colored material so as to reduce the likelihood of misplacement.

In certain other aspects, other solutions exist involving multi-component involving multi-component assemblies that screw and/or hinge together with seals that prevent water ingress. A plug may be used that fits within the distal potion of the connector in which the electrical contacts are disposed. Alternatively, a rolled tube with a closed end could be unrolled over the connector to provide protection. This tube may be formed of an elastomeric material, such as rubber or other material that is suitably flexible and/or rollable. The tube may be designed to be reusable or disposable. In one aspect, an internal sponge to absorb moisture that may leak into the sealed area of the disposable item. In use of some plugs or caps, a tight fit between the connector and cavity may form a vacuum which could draw in water or moisture. To address this issue, one approach is to break the seal and release the suction away from the trapped water so that it is not drawn into the connection. Other options include removal of the trapped water by other means such as an anti-rotation feature on the plug that would necessitate unthreading of the nut. The plug could be used with grease or other substance that would act as a barrier to moisture ingress. In another approach, additional features could be added to the plug that would lengthen the path ingressing water would need to travel to reach the critical hardware.

While various aspects and features have been described above, it is appreciated that the invention can be applied to any cable connector or other item with fluid sensitive critical features that can be inserted into the cap such that a seal is created around the item isolating the sensitive area from the non-sensitive area. In certain aspects, the protective cap comprises a single piece molded construction, a fluid seal, push-on and pull-off installation and removal, and an integral leash features. The protective cap and tether may be made from a soft and highly flexible material promoting compliance to varying geometry, ease of use, patient comfort and biocompatibility. The protective cap can be fabricated from a brightly colored material so as to reduce the likelihood of misplacement.

BRIEF DESCRIPTION OF THE DRAWINGS

FIG. 9 shows a side view of a protective cap having a tether in accordance with aspects of the invention.

FIG. 10A shows a cross-section of a body portion of the protective cap of FIG. 9.

FIG. 10B shows a view of a distal end of the body portion of the cap of FIG. 9.

DETAILED DESCRIPTION OF THE INVENTION

Figure 1:
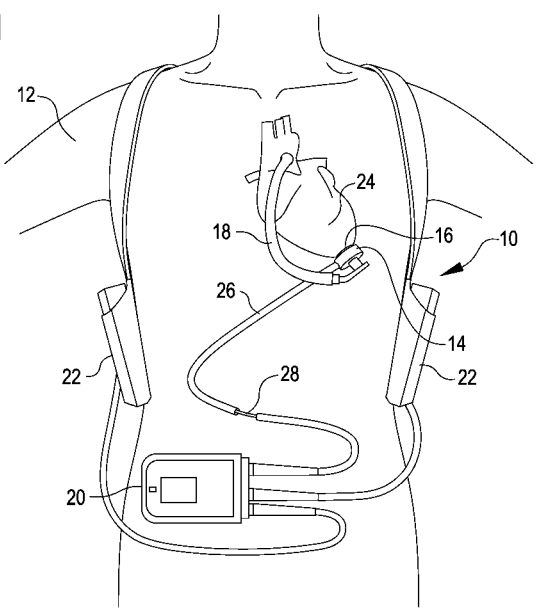
FIG. 1 is an illustration of a mechanical circulatory support system implanted in a patient's body.
Figure 2:
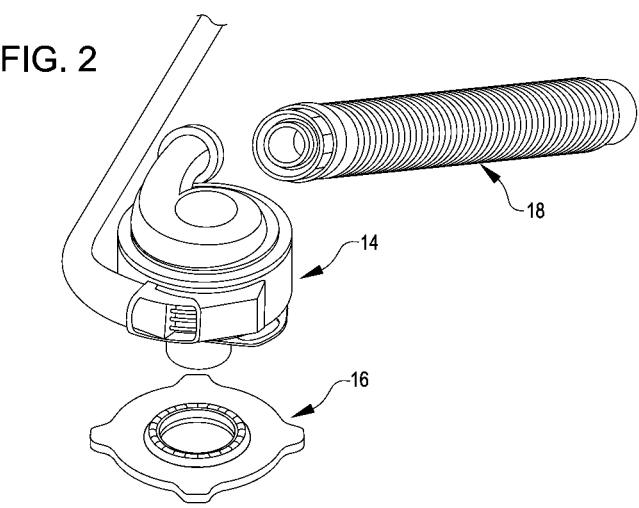
FIG. 2 is an exploded view of certain components of the circulatory support system that are implanted in a patient's body.

FIG. 1 is an illustration of a mechanical circulatory support system 10 implanted in a patient's body 12. The mechanical circulatory support system 10 comprises a implantable blood pump 14, ventricular cuff 16, outflow cannula 18, system controller 20, and power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. With reference to FIGS. 1 and 2, the blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline connects the implanted blood pump 14 to the system controller 20, which monitors system 10 operation. The driveline includes a percutaneous portion 26 that exits the patient through an abdominal aperture 29 and terminates at in-line connector 28 that connects the percutaneous portion 26 with the modular external cable 27, the other end of the modular cable being protected within the system controller, item 20 in FIG. 1. Prior to that connection of the percutaneous cable 26 and the modular cable 27 being made in the operating room, a cap or cover in accordance with the present invention may be installed over the free end of the modular cable 27. An example of such a driveline having an in-line connector with which the cap may be used is described in detail in U.S. application Ser. No. 13/314,806, the contents of which are incorporated herein in their entirety for all purposes. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood bump 14. Examples of such modifications are further described in U.S. Pat. No. 8,562,508 and U.S. Patent Publication No. 2013/0127253, all of which are incorporated herein by reference for all purposes in their entirety.

Figure 3:
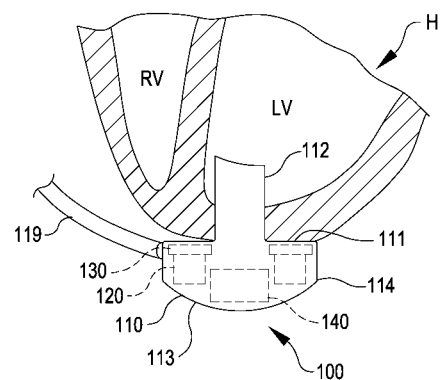
FIG. 3 is an illustration of a blood pump in an operational position implanted in a patient's body.
Figure 4:
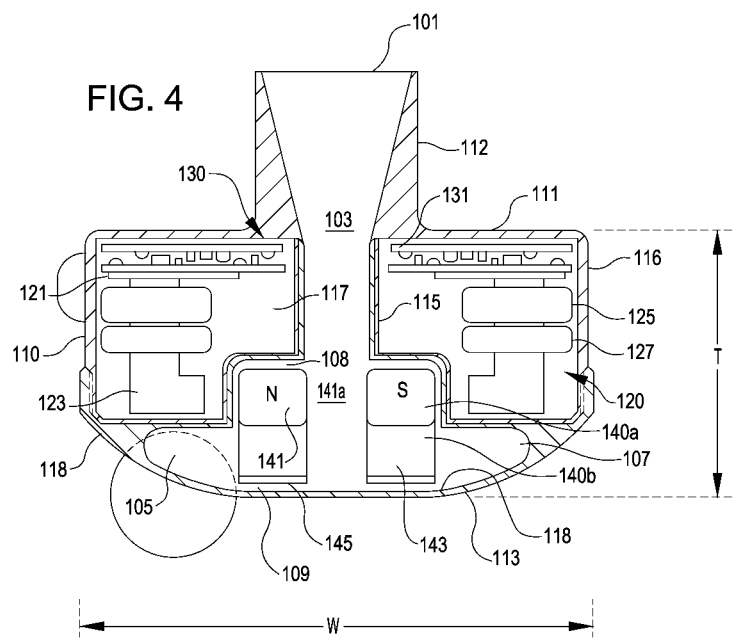
FIG. 4 is a cross-sectional view of the blood pump of FIG. 3.
Figure 5:
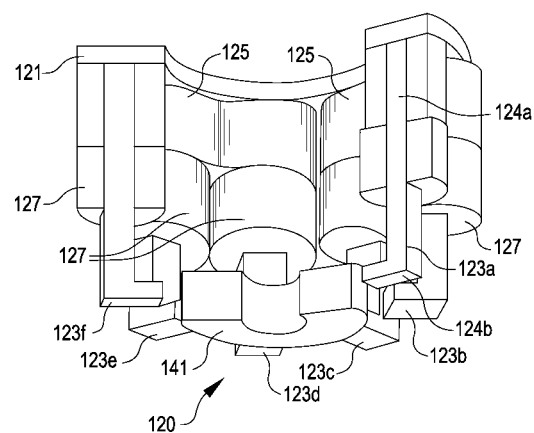
FIG. 5 is a partial cut-away perspective view of a stator of a blood pump.

With reference to FIGS. 3 to 5, a left ventricular assist blood pump 100 having a circular shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113. This positioning of the stator 120, electronics 130, and rotor 140 permits the edge 114 to be chamfered along the contour of the rotor 140, as illustrated in at least FIGS. 2-4, for example.

Referring to FIG. 4, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the pump 100 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIGS. 4 and 5, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 may include a Hall sensor that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g. the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor may sense a current position of the rotor 140 and/or the permanent magnet 141, wherein the output voltage of the Hall sensor may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

Figure 6A:
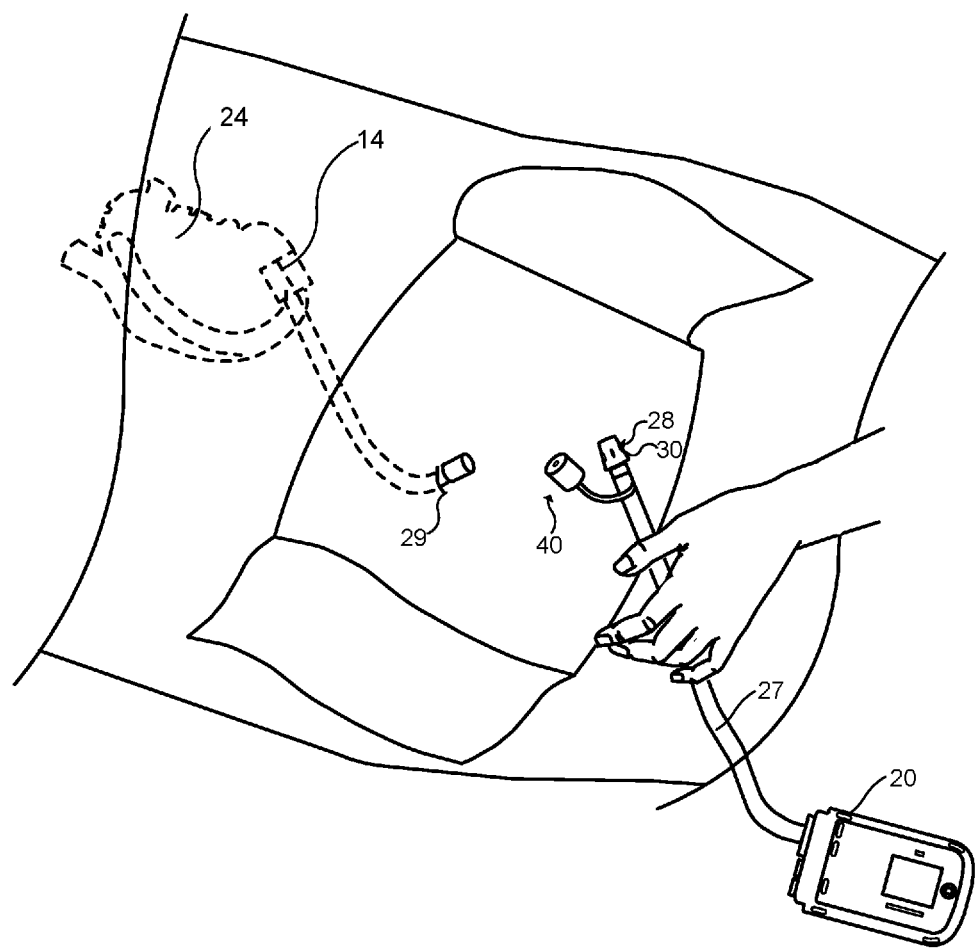
FIG. 6A is an overview of a protective cap being used by a surgeon in an implantation procedure of a circulatory support system to protect an in-line connector of a modular cable of the driveline cable in accordance with aspects of the invention.

FIG. 6A illustrates a surgeon using a protective cap 40 in accordance with aspects of the present invention with an in-line connector of a modular driveline cable. The protective cap is particularly useful to protect the connector 30 of the in-line connector 28, the cap having been removed to facilitate connection between the modular cable 27 and the percutaneous cable portion 26 of the driveline. It is appreciated that similar caps could be used to protect various other connectors such as the in-line connector of the percutaneous cable portion 26 or any other connector for which fluid sealing is desired.

Figure 6B:
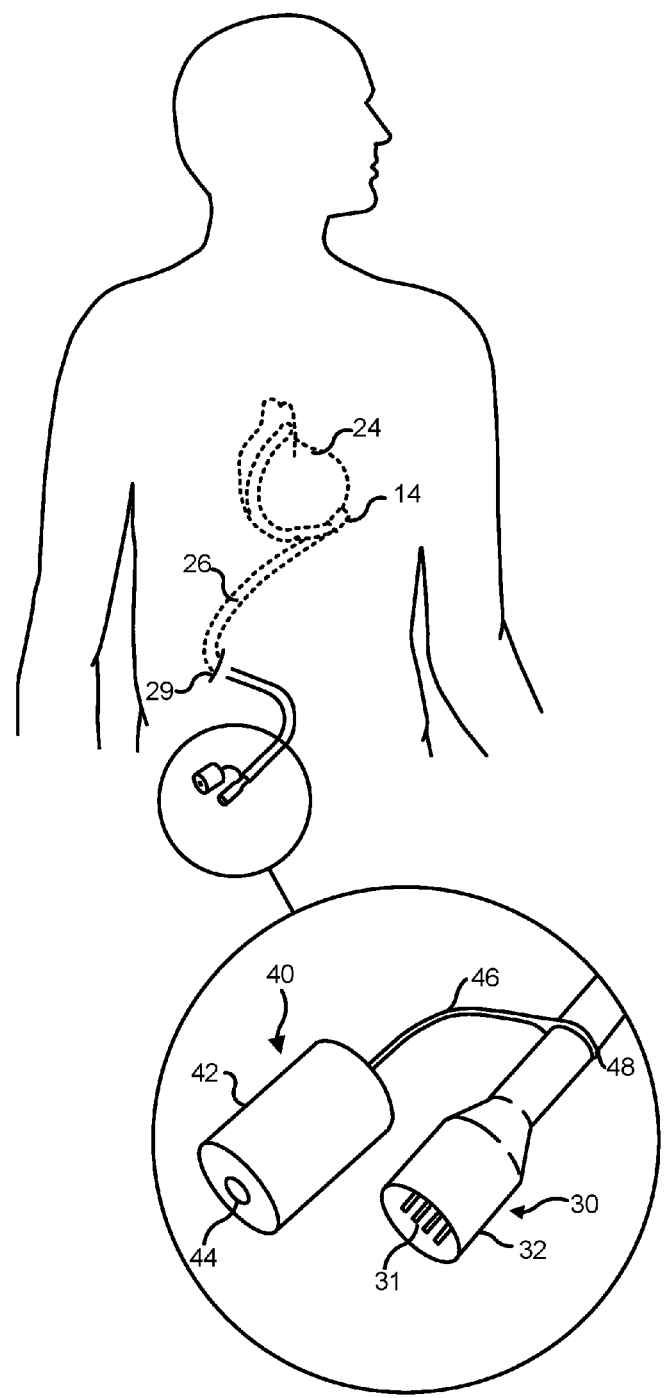
FIG. 6B is an overview of an implanted circulatory support system having a driveline with an external portion having a connector and tethered protective cap in accordance with aspects of the invention.

FIG. 6B illustrates a circulatory support system having VAD with a blood pump 14 implanted in the patient's heart 24 that is powered by a driveline cable 26 that extends outside the patient from an aperture 29 in the patient's abdomen (without the in-line connector described above). The driveline cable 26 terminates in a distal connector 30 adapted to couple with a corresponding connector of an external power source and/or control unit (as shown in FIG. 1). In the embodiment shown, the connector 30 is a connector plug 32 having a plurality of electrical contacts 31 and various associated electrical components disposed therein (not shown). The distal portion of the driveline cable includes a protective cap 40 for protecting a connector 30 of the driveline cable. In accordance with aspects of the invention, the protective cap 40 includes a body portion 40 having a cavity disposed therein with a single distal opening 44 through which the connector is inserted and a tether 46 attached to the cap at one end and attached to the cable with a coupling feature or ring 48 at an opposite end. While this example is illustrated in terms of an alternative driveline cable design, it is appreciated that such a cap may be used on a corresponding connector in various other designs of driveline cables, including those having an in-line connector. For example, a cap in accordance with the above described aspects may be used on any connector for which fluid sealing is desired, whether by a patient, surgeon or another party.

Since it is vital to maintain the integrity of the electrical connection between the connector and the power source/control unit to ensure proper operation of the VAD device, it is important that the electrical contacts and associated internal components of the connector remain free from exposure to debris and fluids, which can damage the sensitive internal contacts or degrade the electrical contacts. As described above, the connector may be exposed during implantation of the VAD or when a patient disconnects the connector to bathe or shower. Use of a cap within this context may refer to a fully or partially implantable transcutaneous energy transfer system, such any as those described in the references incorporated by reference herein.

While conventional cable connectors utilize various covers and caps to protect connectors, such caps are often designed to mimic the design of the corresponding connector, which may require costly and more complicated designs. Furthermore, such design may not adequately seal the connector since the connections are not typically designed to be used within a shower or a wet environment. While caps having screw-on threads have been proposed to provide improved sealing, threads may also provide a path for fluid and moisture to infiltrate into the cap such that when threaded caps are used, saline used during VAD implantation or water from showering may still eventually infiltrate into the cap and damage the connector. While various other sealing mechanisms have been proposed, mechanisms that provide improved sealing often utilize multiple components and/or require multiple steps or manual operation of moving parts that may lack durability and unnecessarily complicate installation of the cap requiring manual dexterity which many elderly patients lack.

In certain aspects, the protective cap overcomes these drawbacks associated with conventional caps and covers by sealing at the connector (at least a distal portion) within an internal cavity by sealing engagement of a flexible ridge circumscribing a distal opening of the cavity about a portion of the cable proximal the connector. Advantageously, this configuration facilitates ease-of-use, particularly by elderly patients, by allowing installation and removal of the protective cap by a manual pushing or pulling movement, thereby avoiding movement requirement more dexterity such as screwing of threads or manipulation of more complex sealing mechanisms, which can be more costly, less reliable and less user friendly.

In one aspect, the protective cap seals the entire connector within a single cavity upon insertion of the connector into the cavity through a single distal opening. The connector is fluidly sealed within the cavity by sealing engagement between a flexible annular ridge circumscribing the single distal opening and a proximal portion of the cable or an associated component such as a sleeve or boot member disposed over the cable and/or proximal portion of the connector.

Figure 7:
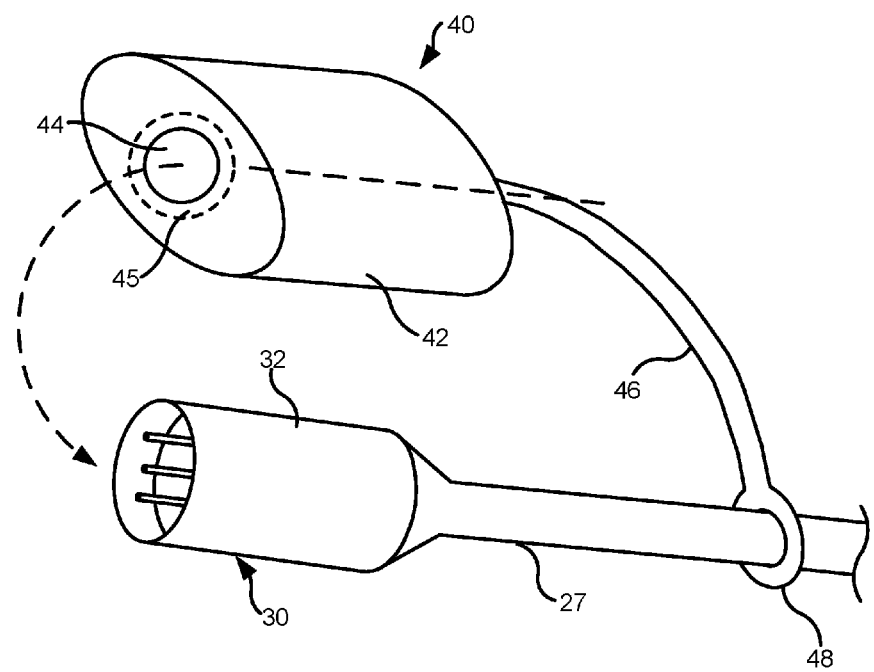
FIG. 7 shows a detail view of a protective cap tethered to a distal portion of a cable near a connector in accordance with aspects of the invention.
Figure 8:
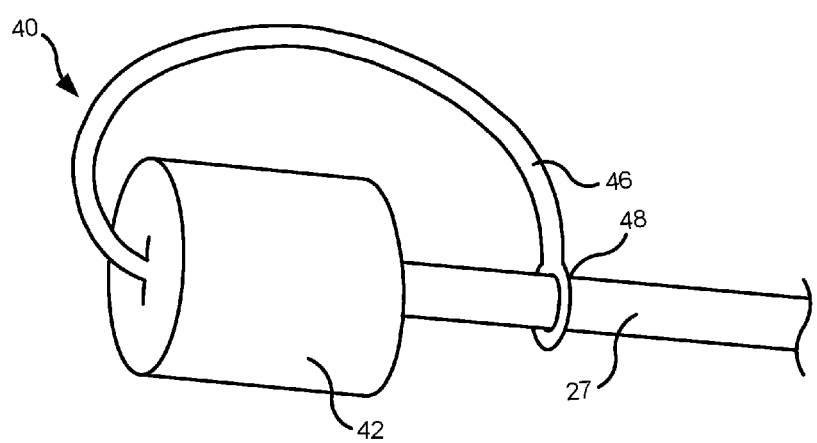
FIG. 8 shows a detail view of a connector of a cable sealed within a protective cap tethered to a distal portion of a cable in accordance with aspects of the invention.

FIGS. 7 and 8 illustrate a connector 30 of a driveline cable 26 having an protective cap 40 tethered to the cable in accordance with certain aspects of the invention. FIG. 7 illustrates the protective cap 40 before being installed over the connector 30. A user may manually push the protective cap 40 over connector along a longitudinal axis of the cap, or alternatively insert the connector into the cavity through the distal opening 44. The distal opening 44 is defined by a flexible annular ridge 45 that deflects or stretches so as to receive the connector 30 within the cavity 41 (see FIG. 10A). The coupling feature or ring 48 of the tether 46 maintains the protective cap near the connector for convenience and ease of use. The coupling ring 48 may be configured to allow the protective cap 40 to slide to facilitate installation, or alternatively it may be configured to attach the tether to a particular location on the cable. In one aspect, the tether or leash 46 is integrally formed with the protective cap body portion 42 from a common material. This aspect is advantageous over multi-part caps, since the lack of separate parts simplifies the fabrication and design of the protective cap, as well as reduces production costs and improves durability of the component. As shown in the embodiment of FIG. 8, when the protective cap is installed on the connector 30, the connector is disposed entirely within the cavity and the annular ridge is sealingly engaged with the cable or associated component so that the connector is fluidly sealed within the cavity.

FIG. 9 illustrates a detailed side view of a protective cap and FIGS. 10A-10B illustrate cross-sectional views of the body portion of the protective cap in accordance with embodiments of the invention. The protective cap 40 includes the main body portion 42 and a tether extending from the main body portion to a proximal coupling feature 48 defined by a ring through which the cable extends. The inside diameter d of ring may be dimensioned to be about the same as the outside diameter of the cable so that the protective cap 40 remains tethered to a particular location or may be dimensioned slightly larger than the cable diameter so that the protective cap remains slidable or movable as desired, which may improve patient comfort. In one aspect, the outside of body portion 42 of the protective cap 40 has an oval cross-section about 1"×0.65" and an overall length of about 1.3," the cylindrical cavity inside is about 0.6" in diameter and 1.2" in length, and the distal opening being about 0.355" and the flexible annular ridge having a thickness of about 0.03" and thinning as the ridge extends inwardly toward the longitudinal axis. The tether is about 5" long and has a thickness (t) of about 0.05" and a width (w) of about 0.1", while the coupling ring 48 has an outer diameter of 0.45" and an inside diameter of about 0.35." It is appreciated that these dimensions of the protective cap 40 correspond to the dimensions of the driveline cable and connector with which the protective cap is used and that various other dimensions may be used depending on what type and size of connector is being sealed. In certain aspects, the protective cap may be used with end connective and driveline cables of varying sizes and shapes so long as the flexible annular ridge fluidly seals the connector (or at least a distal portion thereof) within the cavity of the protective cap to protect the connector and the internal components from debris and fluids.

Figure 11A:
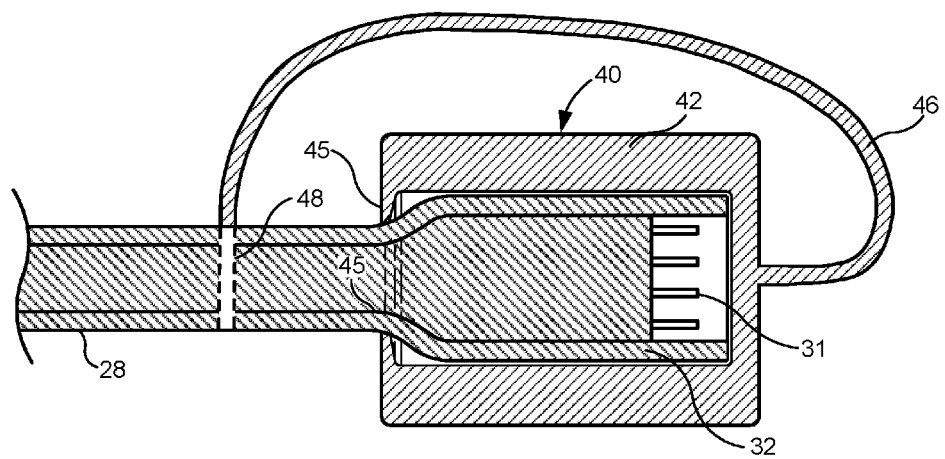
FIG. 11A-11B show cross sectional views of a connector sealed within a protective cap in accordance with aspects of the invention.
Figure 11B:
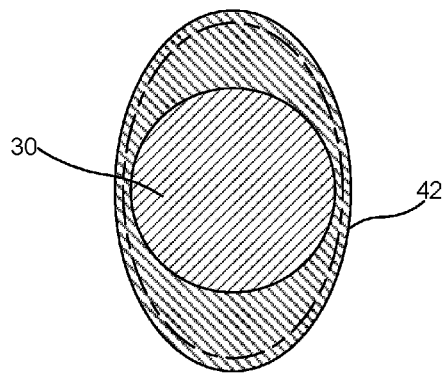

FIGS. 11A-11B illustrate cross-sectional views of a protective cap 40 installed on a connector 30 in accordance with embodiments of the invention. FIG. 11A illustrates a cross-sectional view taken along the longitudinal insertion axis of the protective cap while FIG. 11B illustrates a cross-sectional view perpendicular to the longitudinal insertion axis. As shown, the cavity is dimensioned to fittingly receive the connector 30 within and the flexible annular ridge 45 is dimensioned to sealingly engage with a portion of the cable proximal the connector to entirely circumscribe the cable so as to fluidly seal the entire connector within the cavity. While in this embodiment, the cavity is dimensioned to correspond to a particular size and shape of the connector, in other embodiments, the cavity could be formed in a variety of shapes that do not necessarily correspond to a size or shape of the connector being sealed, but such embodiments would still be effective so long as the flexible annular ridge provides a fluid seal that entirely circumscribes the cable or associated component proximal of the connector portion being sealed.

In certain aspects, a protective cap in accordance with the invention may include various other features adapted to protect the electrical contacts of the connector when disposed within the cavity. Such features may include a particular dimensioning or shape of the cavity, one or more flexible ridges or molded features, air flow ports to reduce suction, absorbent material to absorb splashed fluid, tape or grease to prevent trapped water, and other features which will be understood by one of skill from the description herein. Such features may be configured for displacing residual fluid, directing fluid away from the connector, or reducing suction created during removal of the connector from the cap. In addition, it is appreciated that a protective cap may be configured with any of the above noted features or any combination thereof.

Figure 12:
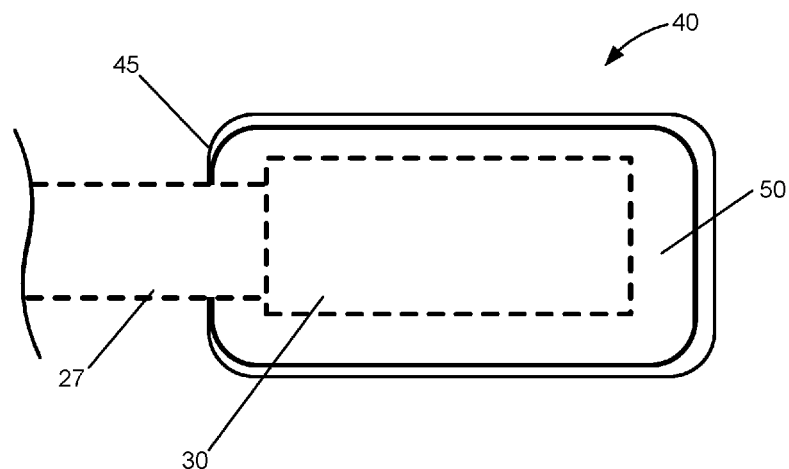
FIG. 12 shows an example protective cap disposed on an in-line connector of a driveline cable, in accordance with aspects of the invention.

In one aspect, the suction created by removing the connector from the protective cap can be reduced by increasing the volume of the protective cavity in which the connector resides. By increasing the cavity volume, the change in volume upon removal of the connector is reduced such that any reduction in pressure during removal is reduced. For example, as shown in FIG. 12, the protective cap 40 may be dimensioned to increase the volume of the cavity substantially beyond that needed to house the connector 30. As shown, there is an additional void 50 in the cavity when the connector 30 is sealed within the cavity. The cap could be dimensioned so that the void 50 is located at one end or merely scaled larger so that the void is distributed equally about the connector. It may be advantageous to dimension the cavity so that the void 50 is at the end of the cavity since this avoids an excessive outer dimension of the cap and also increases the splash length of the cavity so that any fluid drawn into the cavity would be less likely to splash onto the contacts of the connector during withdrawal. In certain embodiments, the cap is dimensioned so that the connector occupies about 80% or less of the volume of the cavity. This ratio can selected to further reduce the suction created as desired. For example, dimensioning the cap so that the connector occupies about 75%, 60%, 50% or less of the volume of the cavity incrementally reduces the suction created. In an exemplary embodiment, however, the cap is dimensioned so that the connector occupies between 60% and 80% so as to reduce suction sufficiently yet avoid unnecessarily increasing the overall size of the cap.

Figure 13:
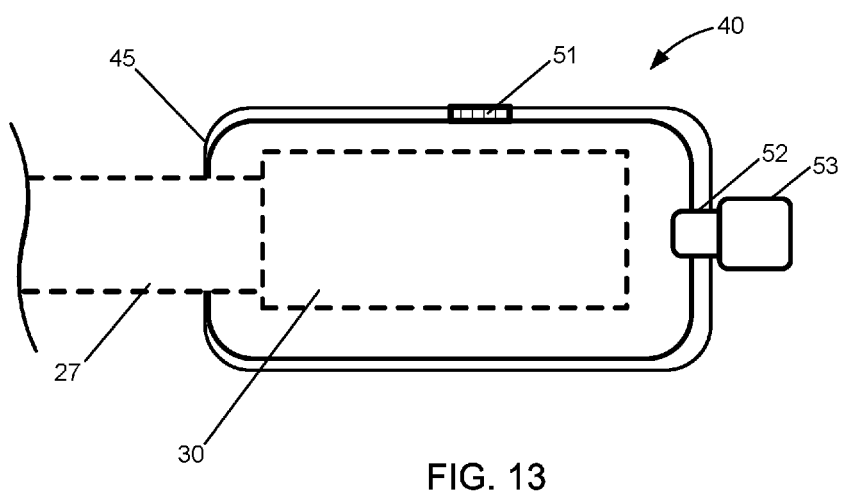
FIG. 13 shows an example protective cap disposed on an in-line connector of a driveline cable, in accordance with aspects of the invention.

In another aspect, the protective cap may include one or more holes, ports or air permeable portions, vents or valves that allow pressure within the cavity to be equalized as the connector is withdrawn from the cavity. As shown in FIG. 13, a protective cap 40 may include a vent or air permeable membrane 51 that is sealed against flow of water but allows air flow when suction is created within the cavity. The protective cap 40 may also include a port 52 that is plugged with a removable plug 53 so that a user can remove the plug 53 before withdrawing the connector. In some embodiments, the cap may include one or more holes, such as pinholes, that are sufficiently small to prevent flow of fluid therethrough but sufficiently large enough to allow air flow when a suction is created within the cavity. In many applications, the cap is only required to be resistant to water (e.g. blast resistant under an IPX 4 standard) such that small holes provide satisfactory sealing against fluids.

Figure 14:
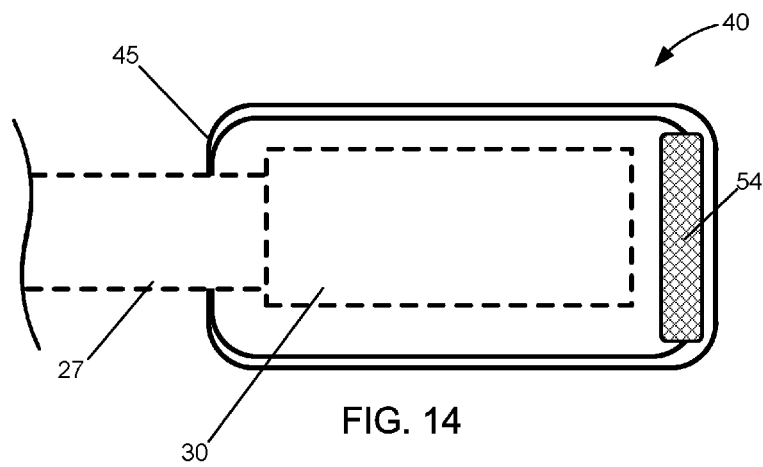
FIG. 14 shows an example protective cap disposed on an in-line connector of a driveline cable, in accordance with aspects of the invention.

In yet another aspect, the protective cap may include an absorbent material, such as a sponge, to absorb any fluid that may be drawn into the cap when the connector is removed. Positioning the absorbent material at the end of the cavity is advantageous as it ensures that fluid drawn into the cavity does not splash against the end of the cavity and onto the pins of the connector as it is withdrawn. As shown in FIG. 14, the absorbent material may be a sponge 54 disposed along the relatively flat closed-end of the cavity.

Figure 15:
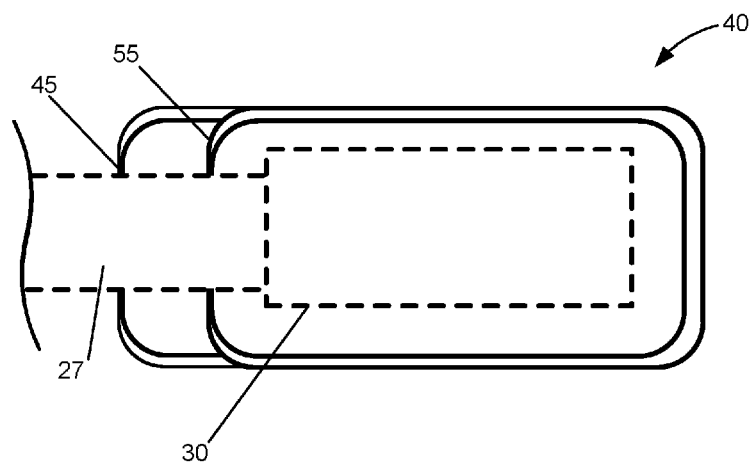
FIG. 15 shows an example protective cap disposed on an in-line connector of a driveline cable, in accordance with aspects of the invention.

In certain aspects, the protective cap may include additional molded elements or seals such that upon breaking of a first seal, any fluid drawn into the cap is trapped or deflected by the molded elements or another seal. As shown in FIG. 15, the protective cap 40 includes an additional seal 55 so that when any fluid drawn into the cavity upon breaking of the seal formed by the flexible outer ridge 45 is sealed or defected by feature 55. In some embodiments, the secondary molded element does not seal but merely is configured so that fluid is deflected by the molded element. It is appreciated that this feature may be configured and shaped in a number of different ways towards these ends.

Figure 16:
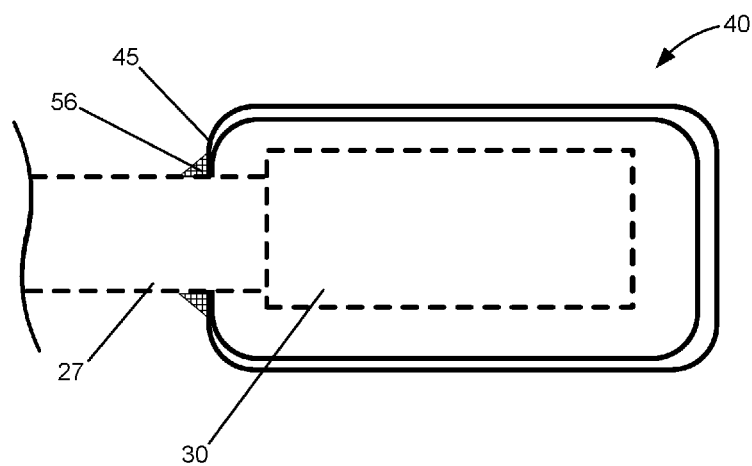
FIG. 16 shows an example protective cap disposed on an in-line connector of a driveline cable, in accordance with aspects of the invention.

In certain other aspects, the protective cap may be used with a means to remove or prevent residual water from collecting at the interface of the seal formed by the flexible ridge 45. For example, compressed air may be used to remove any fluid, either applied by a user or by an action of the cap. In some embodiments, such as that shown in FIG. 16, a fluid barrier 56 is used to prevent build-up of fluid at the seal. The fluid barrier may include a jelly, grease, or Teflon tape. The fluid barrier may be pre-applied along with the cap to the connector such that a user would receive the drive-line cable with the cap and barrier in place so as to prevent fluid buildup as well as the potential for splashback of fluid onto the pins of the connector during removal of the cap. The fluid barrier may be supplied with the in-line connector in a heat sealed package.

Figure 17:
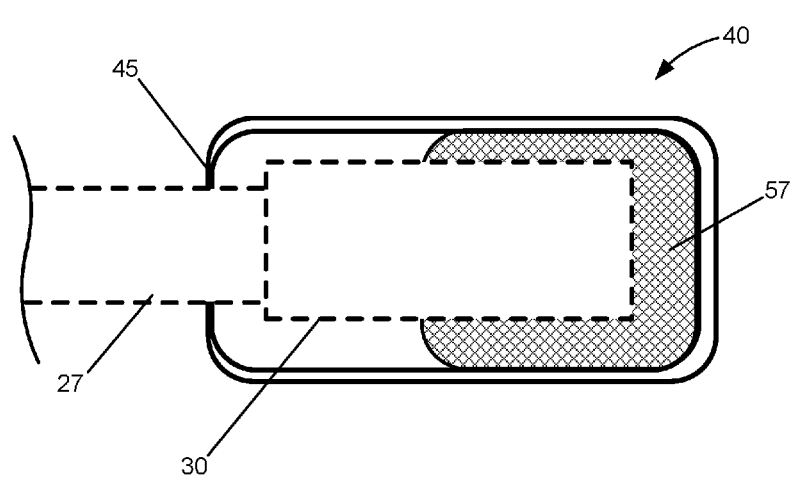
FIG. 17 shows an example protective cap disposed on an in-line connector of a driveline cable, in accordance with aspects of the invention.

In another aspect, the cap may include a protective contact block molded to interface with the distal portion of the connector. In some embodiments, the contact block may be shipped loose with the connector plug and a tunneling adapter to be installed first as a contact block protector. The contact block may be molded as a look-alike component to the corresponding connector, which is advantageous because this would not require any change to the connector plug or adapter. For example, as shown in FIG. 17, the protective contact block 57 may be molded to mimic the in-line connector end of the percutaneous cable and engage with the connector when disposed within the cavity such that the connector remains protected from any splashed fluid drawn into the cavity during removal. The protective contact block 57 may be fixedly attached within the cavity or may be a separate component. When configured as a separate component, the cap may be configured so that complete removal of the cap also removes the protective contact block, which may remain loose within the cavity. Providing the protective contact block 57 loose within the cavity may be advantageous as it may allow the block to remain attached to the connector as the connector is withdrawn until the seal formed by flexible ridge 45 is broken. Further removal of the connector may cause the ridge around the opening of the cavity to withdraw the protective contact block 57 from the connector. In some embodiments, a second molded element may be included that has it's own seal and is adapted to function like a piston so that the second molded element can be withdrawn in various configurations so that suction is broken away from the trapped reservoir of fluid and away from the contact block.

Figure 18:
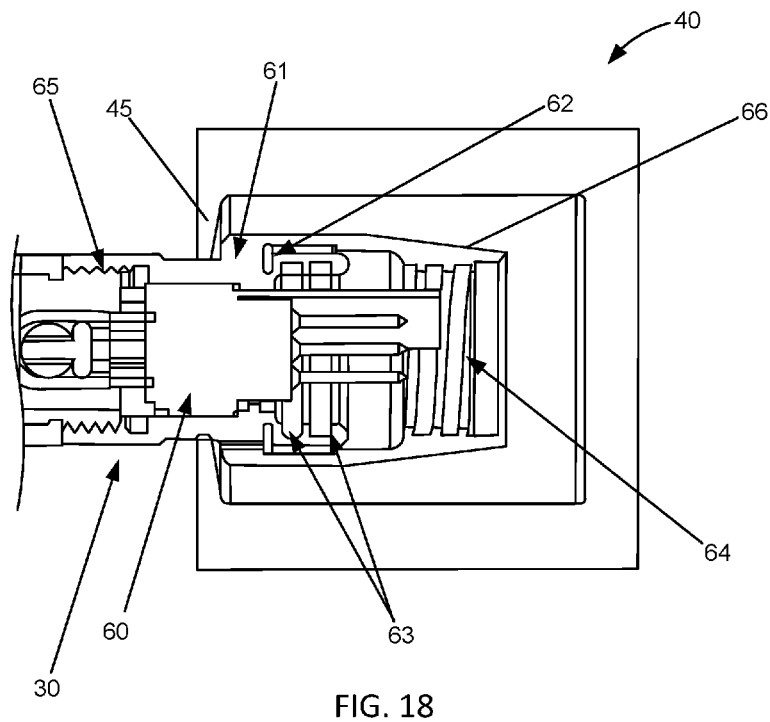
FIG. 18 shows an example protective cap disposed on an in-line connector of a driveline cable, in accordance with aspects of the invention.

In another aspect, the protective cap 40 may be configured for use with an in-line connector 30 having a retention assembly that allows air flow into the cavity during removal of the connector from the cap 40. For example, as shown in FIG. 18 the in-line connector 30 includes a contact block 60 from which the connector pins extend. The in-line connector 30 further includes screw threads 65 that couple with the modular driveline cable, screw threads 62 for coupling with the percutaneous cable connector, two O-rings 63 to provide fluid sealing of the electrical connection when coupled with the percutaneous cable, and a C-ring 62 that retains the rotatable nut 66 of the connector. Nut 66 is free to rotate so as to allow the threads 64 to tighten with a corresponding connector of the percutaneous cable without twisting of the cables. An air gap 61 is provided under the nut 66. The protective cap 40 may be configured so that the flexible ridge seal 45 provides sealing against the body of the in-line connector 30 just proximal of the rotatable nut 66. In some embodiments, the thickness of the flexible ridge seal 45 at the inner diameter is less than 0.1 inches, such as about 0.030 inches. In one aspect, the inner diameter clearance to the nut 66 outer diameter is greater than about twice the thickest portion of the seal 45 so as to squeeze between the nut outer diameter and the seal inner diameter without requiring undesirably high insertion forces. In the embodiment shown in FIG. 18, this clearance is about 0.18 inches. A substantial margin may be allowed in embodiments where the inner side of the seal is angled, such as that shown in FIG. 18. Angling of the inner side of the seal provides increasing stiffness in the ridge seal as it extends away from the centerline. In some aspects, the angle of the inner side of the seal is relatively low so as to limit this increase in stiffness, for example, an angle less than 30 degrees, such as about 20 or about 10 degrees. The ridge seal may also be formed with a taper on an inside face of the seal to facilitate removal of an inner core during molding of the seal. In another aspect, the side-wall of the cap along an axial length is sufficiently thick to provide axial rigidity during removal of the cap. In some embodiments, the wall thickness of a cap having an outer diameter of about 1 inch is about 0.15 inches, although it is appreciated that differing thickness may provide sufficient rigidity depending on the material of which the cap is formed. In some embodiments, an inside clearance to the nut 66 is configured to allow a full length of seal material to be bent inward behind the nut during insertion. In the example embodiment in FIG. 18, this inside clearance of nut 66 is about 0.16 inches. Upon removing of the connector 30 from the protective cap, the air gap 61 is exposed to the external environment while the flexible ridge remains sealed against the outer diameter of the rotatable nut 66. This configuration allows air flow into the cavity to equalize pressure and avoids fluid being drawn directly into the cavity to avoid splashback of fluid against the distal end of the cavity. In one aspect, the above described configuration is advantageous as it may allow the cap assembly to float if dropped in water. Further advantages of the protective cap 40 may be further realized when used in combination with a particular connector configuration, such as that shown in FIG. 18.

Figure 19:
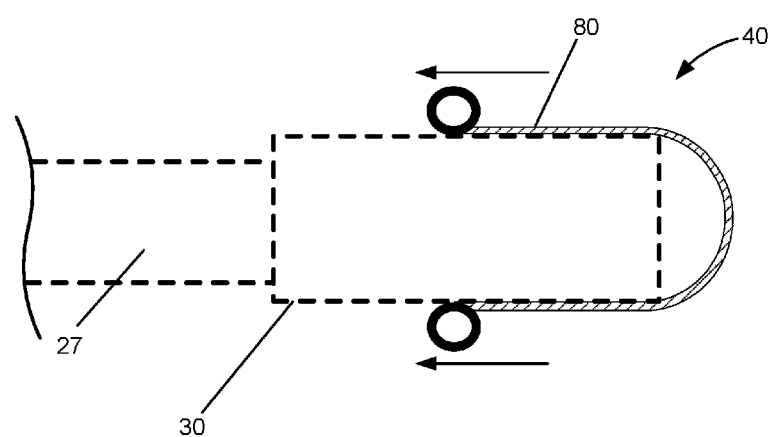
FIG. 19 shows an example protective cap disposed on an in-line connector of a driveline cable, in accordance with aspects of the invention.
Figure 20:
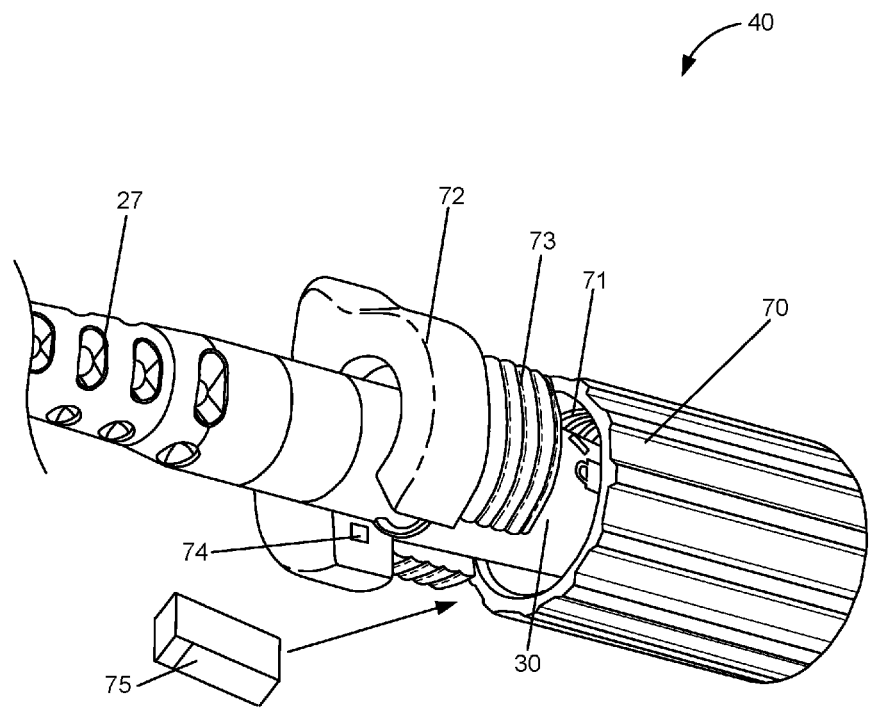
FIG. 20 shows an example protective cap disposed on an in-line connector of a driveline cable, in accordance with aspects of the invention.

In some embodiments, the protective cap may be defined by a flexible material and/or by multiple components that engage one another so as to seal a distal portion of the connector within a protected cavity without requiring the flexible annular ridge noted in the various embodiments described above. For example, as shown in FIG. 19, the protective cap may be formed of an elastic flexible material 80 that can be rolled onto the connector, thereby sealing the connector within by the elasticity of the material 80. Such a cap may be disposable or re-usable and may be formed of a later or polymer material, or any material having sufficient elasticity and durability to provide fluid sealing of the connector. Some embodiments include multiple components that sealingly engage with one another to form a cavity in which the connector 30 is protected. For example, as shown in FIG. 20, the protective cap 40 may include a distal cap 70 having inner threads 71 that engage with corresponding threads 73 of a C-ring 72. The C-ring 72 may include one or more sealing features, such as an O-ring 74, to provide sealing near a proximal end of the connector 30 while the connector 30 is within a cavity formed by the C-ring 72 screwed into the distal cap. The open portion of the C-ring 72 allows for its removal from a more proximal portion of the cable 27. This open portion can be sealed in a variety of ways, such as by an additional sealing feature 75, which may be an entirely separate element or may be incorporated into the C-ring 72 or the cap 70. For example, sealing feature 75 could be slidably contained within the cap and slide into the open portion of the C-ring as it is screwed into place. Alternatively, the sealing feature may be incorporated into the C-ring 72 (e.g. two rotatable C-rings). An additional sealing feature, such as an O-ring (not shown), may be provided on an underside of the enlarged upper portion of the C-ring 72 so as to sealingly engage the C-ring 72 with the distal cap 70 when screwed within so as to form a fluid-tight cavity in which the connector can remain protected from external fluids.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A protective cap for protecting a connector of a cable, the protective cap comprising:
   a body portion having an interior hollow cavity with a distal opening, the cavity dimensioned to receive at least a distal portion of the cable connector inserted through the distal opening along a longitudinal axis of the body portion; and
   a flexible annular ridge circumscribing the distal opening and extending inwardly towards the longitudinal axis such that insertion of the cable connector into the hollow cavity resiliently deflects the flexible ridge so as to seal the at least distal portion of the cable connector within the hollow cavity.

2. The protective cap of claim 1, wherein the cavity is dimensioned so as to substantially receive the entire connector therein and the flexible ridge is dimensioned so as sealingly engage an outside surface of a portion of the cable proximal of the connector.

3. The protective cap of claim 1, wherein the body portion has a substantially oval cross-sectional shape while the distal opening comprises a circular opening and the flexible ridge comprises an annular ridge.

4. The protective cap of claim 1, wherein the cavity is substantially cylindrical so as to receive a substantially cylindrical connector.

5. The protective cap of claim 1, wherein the cavity and flexible ridge are configured such that the connector is fluid resistant when sealed within the protective cap.

6. The protective cap of claim 1, wherein the body portion comprises a resilient material and includes one or more reinforcing portions that provide longitudinal rigidity so as to facilitate insertion of the cable connector into the cavity and withdrawal of the connector therefrom.

7. The protective cap of claim 1, wherein the protective cap is defined as an integral component.

8. The protective cap of claim 1, wherein the protective cap is configured to seal the connector within the hollow cavity without requiring the cap interface with any components other than an outer surface of the cord or the connector.

9. The protective cap of claim 1, wherein the body portion and flexible ridge are integrally formed of a flexible resilient material.

10. The protective cap of claim 9, wherein the flexible resilient material comprises an elastic polymer.

11. The protective cap of claim 1, wherein the cavity and the flexible ridge are dimensioned such that the protective cap is configured to sealingly receive any connector of a plurality of connectors of differing sizes and shapes.

12. The protective cap of claim 1, wherein the protective cap further comprises:
    a tether attached to the body portion at one end and having a coupling feature at an opposite end for coupling with the cable or connector.

13. The protective cap of claim 12, wherein the coupling feature comprises a ring dimensioned to receive the cable therethrough.

14. The protective cap of claim 12, wherein the body portion, the flexible ridge and the tether are integrally formed of a common material.

15. The protective cap of claim 1, further comprising a driveline cable, the protective cap being attached to the drive line cable by a tether.

16. The protective cap of claim 1, wherein the protective cap is dimensioned so that when the connector is sealed within the cavity, the connector occupies about 80% or less of the volume of the cavity.

17. The protective cap of claim 16, wherein the cavity is dimensioned such that when the connector is sealingly disposed within, a majority of an excess space in the cavity is between a distal end of the connector and a closed end of the cavity.

18. The protective cap of claim 1, wherein the body portion includes any of: one or more holes, ports, vents, valves, and air permeable portions that allow a pressure within the cavity to be equalized with a pressure of an environment external the protective cap when the pressure within the cavity is less than the pressure of the external environment.

19. The protective cap of claim 18, wherein the protective cap include a port with a removable plug.

20. The protective cap of claim 1, further comprising:
    an absorbent material disposed within the cavity disposed near a closed end of the cavity.

21. The protective cap of claim 1, further comprising:
    a molded feature inside the cavity that circumscribes the cavity and extends inwardly towards the longitudinal axis.

22. The protective cap of claim 21, wherein the molded feature comprises the flexible annular ridge.

23. The protective cap of claim 1, further comprising:
    a fluid barrier provided at or near the flexible annular ridge.

24. The protective cap of claim 1 further comprising:
    a protective contact block configured to engage the connector while the connector is sealed within the cavity and remain engaged as the connector is withdrawn from the cavity at least until a seal formed by the annular ridge is broken during removal of the connector from the protective cap.

25. The protective cap of claim 24, wherein the protective contact block is a separate component from the protective cap without rigid connection to the protective cap.

26. The protective cap of claim 1, wherein the protective cap is defined by multiple components sealingly engaged with one another.

27. A method of protecting a connector of a cable, the method comprising:
    pushing a protective cap over the connector so as to receive at least a distal portion of the connector within a hollow cavity of the protective cap through a distal opening of the protective cap; and
    sealing the connector within the cavity by advancing the protective cap over the connector until a flexible ridge circumscribing the distal opening sealingly engages about an outer surface of the connector or a portion of the cable proximal of the connector so as to seal the connector from fluid and/or debris in a single sealed cavity.

28. The method of claim 27, wherein advancing the protective cap over the connector comprises manually pushing the protective cap directly onto the connector.

29. The method of claim 27, further comprising:
    removing the protective cap from the connector to facilitate connection between the connector and a corresponding connector of a device.

30. The method of claim 29, wherein removing the protective cap comprises manually pulling the protective cap from the connector.

31. The method of claim 27, wherein the flexible ridge is dimensioned so as to sealingly engage with the outside surface of the portion of the cable proximal the connector when the connector is disposed entirely within the cavity of the protective cap.

32. A protective cap for protecting a connector of a cable, protective cap comprising:
- a body portion having an interior cavity with a distal opening, the cavity dimensioned to receive at least a distal portion of the cable connector inserted through the distal opening along a longitudinal axis of the body portion; and
- a flexible annular ridge circumscribing the distal opening and extending inwardly towards the longitudinal axis such that insertion of the cable connector into the cavity resiliently deflects the flexible ridge so as to seal the at least distal portion of the cable connector within the cavity,
- wherein the protective cap is defined by multiple components sealingly engaged with one another,
- wherein the multiple components comprise a C-ring and a distal cap each having interfacing screw threads and one or more sealing features, wherein the C-ring and distal cap define the cavity when the screw threads are interfaced, and the one or more sealing features provide fluid-tight sealing of the cavity when the connector is disposed within the cavity.

33. A protective cap for protecting a connector of a cable, the protective a cap comprising:
- a body portion having an interior cavity with a distal opening, the cavity dimensioned to receive at least a distal portion of the cable connector inserted through the distal opening along a longitudinal axis of the body portion; and
- a flexible annular ridge circumscribing the distal opening and extending inwardly towards the longitudinal axis such that insertion of the cable connector into the cavity resiliently deflects the flexible ridge so as to seal the at least distal portion of the cable connector within the cavity, wherein the body portion comprises a resilient material and includes one or more reinforcing portions that provide longitudinal rigidity so as to facilitate insertion of the cable connector into the cavity and withdrawal of the connector therefrom, wherein the one or more reinforcing portions comprises opposing portions having increased lateral width.

34. The protective cap of claim 33, wherein the body portion has a substantially oval cross-sectional shape while the cavity has a substantially circular cross-sectional shape such that one or more reinforcing portions of increased width are defined by opposite sides of the body portion at opposing ends of the oval cross-sectional shape.

* * * * *